United States Patent [19]

Grodsky et al.

[11] 4,371,523

[45] Feb. 1, 1983

[54] REDUCING THE AGGREGATION OF INSULIN IN SOLUTION

[75] Inventors: Gerold M. Grodsky, San Francisco, Calif.; Jacques Bringer, Montpellier, France

[73] Assignee: The Regents of the University of California, Berkeley, Calif.

[21] Appl. No.: 220,779

[22] Filed: Dec. 29, 1980

[51] Int. Cl.³ ............................................. A61K 37/26
[52] U.S. Cl. ..................................................... 424/178
[58] Field of Search ......................................... 424/178

[56] References Cited

U.S. PATENT DOCUMENTS

| | | | |
|---|---|---|---|
| 2,190,137 | 2/1940 | Sahyun | 424/178 |
| 2,343,625 | 3/1944 | Abramson et al. | 424/178 |
| 3,868,357 | 2/1975 | Smyth et al. | 424/178 |

OTHER PUBLICATIONS

Diabetologia by Springer-Verlag 1980, "Insulin Aggregation in Artificial Delivery Systems", by W. D. Lougheed et al., v. 19, pp. 1–9.

Primary Examiner—Frederick E. Waddell
Attorney, Agent, or Firm—Phillips, Moore, Lempio & Finley

[57] ABSTRACT

A method for reducing aggregation of insulin within aqueous insulin solutions comprising including in said insulin solutions an anti-aggregation agent selected from pharmaceutically acceptable organic compounds having at least two carboxylic acid moieties and at least one amino, or amino derived, moiety. Such insulin solutions with the anti-aggregation agent are also maintained at pH's approximating the isoelectric point of the anti-aggregation agent. Glutamic acid or aspartic acid are especially preferred as the anti-aggregation agent. Relatively small quantities of such agents prevent, or greatly reduce aggregation of insulin even when such insulin solutions are maintained at elevated temperatures and under agitation for extended periods of time.

12 Claims, 2 Drawing Figures

Insulin Subcutaneously Infused (via Minipump) in the Diabetic Chinese Hamster

Insulin Intraperitoneally Infused (via Minipump) in the Diabetic Chinese Hamster

REDUCING THE AGGREGATION OF INSULIN IN SOLUTION

The invention described herein was partially supported by a grant from the Dept. of Health and Human Services.

BACKGROUND OF THE INVENTION

For a great many years, therapy for those individuals suffering from diabetes mellitus has involved the periodic injection of aqueous and/or saline solutions of the protein hormone, insulin. Injections of insulin are necessary to effectuate metabolism of carbohydrates lipids and amino acids in the afflicted individual who does not possess the ability to internally synthesize this vital hormone. It will be appreciated that the injection technique of therapy results in the introduction of large quantities of insulin into the individual on a periodic basis. These periodic doses and subsequent availability in the metabolic process may not necessarially coincide with high carbohydrate, lipid and amino acid levels in the blood stream of the afflicted individual. Therefore, despite the effectiveness of the insulin injections there is still considerable possibility of a "mismatch" between the levels of carbohydrate, lipids, and amino acids in the individual's blood stream and the concurrent availability of insulin to mediate their metabolism.

In recent years techniques have been developed for preparing "extended" suspensions of insulin which, upon injection, release the hormone more slowly into the blood stream. However, even these techniques result in changes in insulin levels in the blood, which levels do not necessarily coincide with the insulin demand for metabolism.

In order to provide the insulin levels metabolically required over extended periods of time, resort has been made to the development of continual or regulated feed directly or indirectly devices which may be permanently attached, either externally or internally, to the body of the individual. Such devices include a reservoir of insulin solution which is fed on a continuing or controlled basis into the blood stream of the individual. Such devices require the reservoir of insulin solution as a source for the introduction of the hormone into the individual.

Although such devices show great promise in overcoming the difficulties referred to above, an unexpected defect has now appeared which threatens the viability, efficiency and acceptability of such devices. Specifically, when insulin solutions are maintained at or about body temperatures e.g. 37° C., and are subjected to agitation by the individual's movements, self aggregation of the insulin occurrs. Aggregation results in the precipitation of insulin complexes from the solution. Such a phenomenon occurs within a relatively short period of time i.e., in the matter of hours to several days under the conditions noted. This precipitation may occur within the insulin reservoir itself and even more importantly, within the catheters utilized to deliver the insulin solution into the blood stream of the individual. It will be readily apparent that such catheters are, of necessity, very small in size and in essence, comprise capillary passages from the reservoir into the tissues of the individual. The aggregation of the insulin therefore tends to collect within the catheter passages and results in their occlusion. The insulin flow is thereby diminished or even stopped. Even if flow continues, the aggregates can be biologically inactive.

A number of investigators have addressed this insulin aggregation problem. Perhaps the best review of the state of the art is the article by Lougheed et. al. published in *Diabetologia*, 19, pages 1–9 (1980) and entitled "Insulin Aggregation in Artificial Delivery Systems". This article reviews all of the relevant literature to date, discusses the various factors considered to affect the aggegation of insulin solutions; reviews the results of several experiments; and attempts to stabilize insulin solution by the addition of a rather broad spectrum of supplemental materials such as ethylene diamine tetraacetic acid (EDTA) sodium bicarbonate, sodium chloride, cysteine, benzol alcohol, hydrochloric acid, histidine, sodium phosphate, glycine, etc. All such materials, however, do not appear to have any appreciable effect in preventing the aggregation of insulin in solution over extended periods of time. Albisser et. al. in *Diabetes*, 29, pages 241–243 (1980) have reported that the addition of serum to insulin solutions promotes solubilization. However, the problems of supply, purification, and potential protein reaction would indicate that such an approach is not entirely practical at this time.

Thus, up to the present time, the problem of the aggregation of insulin in solutions maintained at body temperature, and under conditions of agitation, seriously threatens the viability of artificial pancreatic devices intended to operate over time periods exceeding several days.

BRIEF SUMMARY OF THE INVENTION

The present invention presents methods for reducing and/or eliminating the aggregation of insulin in aqueous solutions which are maintained at body temperature and under agitation over extended periods of time. Minimization of aggregation is achieved by adding to the insulin solution small amounts of anti-aggregation agents; and further maintaining said insulin solution at a pH approximately equivalent to the isoelectric point of the anti-aggregation agent. More specifically, the effective anti-aggregation agents are organic compounds having at least two carboxyl moieties and at least one amino, or amino derivative, moieties. Most preferably such anti-aggregant agents are dicarboxylic amino acids, specifically aspartic acid and glutamic acid.

Such anti-aggregation agents exhibit their protective effect when the insulin solutions are maintained at a pH approximating the isoelectric point of the anti-aggregant agent. Thus in the case of aspartic and glutamic acids, the insulin solution is maintained at a pH of from approximately 3–3.5, i.e., at their isoelectric point.

It is therefore an object of the invention to provide a method for preventing, or reducing the aggregation of insulin solutions over extended periods of time.

It is another object of the invention to provide insulin solutions which are stabilized against aggregation of the insulin component.

It is yet another object of the invention to prevent and/or reduce the aggregation of insulin solutions through the addition thereto of anti-aggregation agents.

It is a further object of the invention to stabilize insulin solutions against aggregation of the insulin therein by the addition to said solutions of anti-aggregation agents which are organic compounds having at least two carboxyl moieties and at least one amino moiety.

It is yet another object of the invention to stabilize insulin solutions against aggregation of the insulin therein by the addition of aspartic acid.

It is still another object of the invention to stabilize insulin solutions against aggregation of the insulin therein by the addition of glutamic acid.

Additional objects, advantages, and novel features of the invention will be set forth in the description which follows, and in part will become apparent to those skilled in the art upon examination of the following; or may be learned by practice of the invention. The objects and advantages of the invention may be realized and obtained by means of the instrumentalities and combinations particularly pointed out in the appended claims.

BRIEF DESCRIPTION OF THE DRAWING

The accompanying drawing, which is incorporated in, and forms a part of the specification, illustrates experimental results utilizing the method and solutions of the invention, and, together with the description, serves to explain the principles of the invention. In the drawing.

DETAILED DESCRIPTION OF THE INVENTION

Figure 1:
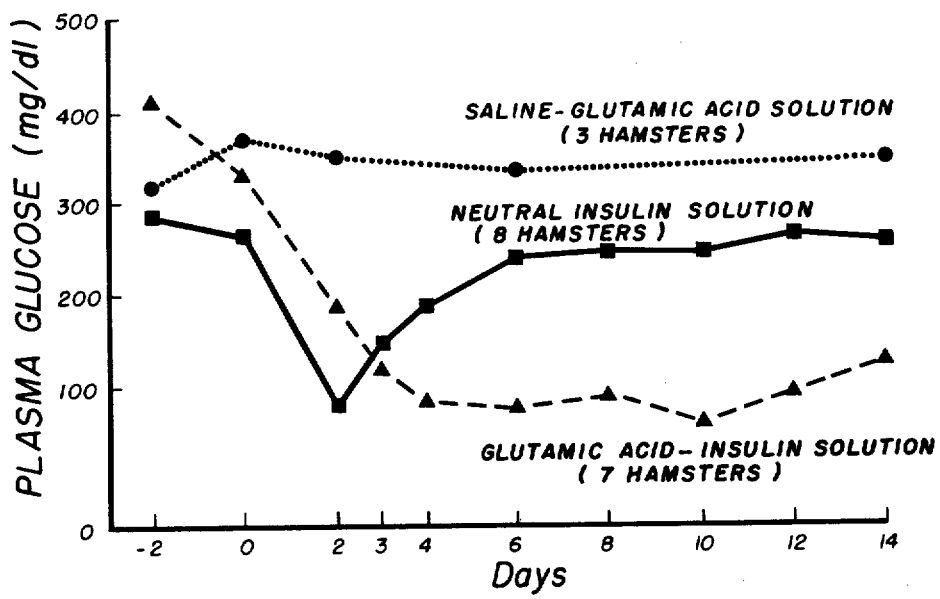
FIG. 1 is a graph presenting data gathered from the subcutaneous delivery of unprotected insulin solutions, and glutamic acid protected insulin solutions, as well as control glutamic acid-saline solutions, to genetically diabetic Chinese hamsters by means of implanted minipumps over a 14 day period.

The method of the invention eliminates and/or reduces the aggregation of insulin in insulin solutions over extended periods of time. Stabilization of the insulin solutions are achieved even though the insulin solutions are maintained at elevated temperatures (in the vicinity of 34°-37° C.) and under relatively constant agitation. Such conditions tend to produce aggregation and subsequent precipitation of insulin from solution. These precipitates reduce the strength of insulin solution which may be delivered from an artificial pancreatic device thereby reducing the quantity of insulin delivered to the host. Perhaps, more importantly, the aggregation of the insulin tends to interfere with, and even prevent the delivery of insulin solution through capillary passages present in artificial pancreatic devices; which capillary passages are necessary in the catheter portions thereof.

More specifically, insulin solutions are stabilized against aggregation by the addition of an anti-aggregation agent to the solution. Such anti-aggregation agents are organic molecules having at least two carboxylic acid moieties and at least one amino moiety. The amino acids, aspartic acid and glutamic acid are especially preferred as anti-aggregation agents.

These anti-aggregation agents may be added to the insulin solutions in relatively small concentrations, e.g., 7 mg/ml in an insulin solution having approximately 50 U per ml. The concentration of anti-aggregation agent in the insulin solutions is not critical. Obviously, sufficient agent must be present to produce the desired effect. It is also desirable to provide sufficient agent, or additional acid, e.g., HCl, in the case of the dicarboxylic amino acids, to reduce solution pH to the agent's isoelectric point.

It has been determined that when dicarboxylic amino acids are added to insulin solution and the solution is maintained at a pH approximating the isoelectric point of the added agent, aggregation of the insulin is eliminated and/or very greatly reduced for extended periods of time. This reduction is effected even though the insulin solutions are maintained at elevated temperatures (about body temperature) and are continually agitated; which conditions have been found to be most conducive to the aggregation and precipitation of insulin from solution.

Aspartic acid and glutamic acid appear to be particularly effective in protecting insulin solutions from aggregation.

The modality through which the dicarboxylic amino acids prevent or greatly reduce insulin aggregation, is not fully understood. Experiments have determined that even though glutamic or aspartic acids are added to insulin solution, if the pH of the solution is raised appreciably above the isoelectric point (pH 3.3-3.5), i.e., to about pH 7, the protective effect of the agents are no longer apparent. It is further believed that the protective effect is not merely the result of a buffering action by the acidic amino acids. Thus when mineral acid, e.g., hydrochloric, or organic acids, such as citric, lactic and acetic, were added to insulin solutions maintained at pH 3.3 to 3.5, a comparable protective effect was not noted. In addition, none of the naturally occurring amino acids were effective at neutral pH's (pH 7.4); nor at acid pH's (pH 3.3-3.5), with the exception of aspartic or glutamic acid. Thus when glycine, lysine, alanine, cystine, valine, serine, threonine, methionine, arginine, phenylalanine, tryptophan, proline, leucine, histidine, asparagine, and glutamine were added, even at acid pH's no protective effect was noted.

It is postulated that the anti-aggregation effect is somehow related to the ability of the added agent to chelate with zinc which is present in the most commonly utilized pharmaceutical forms of insulin. On the other hand, additional experiments have indicated that the dicarboxylic amino acids are also capable of producing the anti-aggregation effect in solutions in which the insulin is present in the sodium, rather than in the zinc form. Thus the mechanism by which the dicarboxyclic amino acids prevent aggregation is still an enigma. Suffice it to say, however, despite the mechanism involved, the presence of dicarboxyclic amino acids in insulin solution greatly inhibits and, in some instances, even eliminates insulin aggregation for extended periods of time.

Both in vivo and in vitro experiments have been conducted in order to demonstrate the preparation of, and the effectiveness of, insulin solution having the anti-aggregation agents therein. Review of the following examples which describe the preparation and utilization of such protected insulin solutions in both in vivo and in vitro application will more clearly illustrate the preparation of such stabilized insulin solution. These examples further illustrate their effectiveness as compared to insulin solutions which were unprotected, or were tested with other additives.

EXAMPLE 1

IN VITRO TESTING

Controlled Shaking of Insulin Solution in Test Tubes

In vitro testing of single component neutral pork zinc insulin was undertaken with a number of added agents. Solutions at about neutral pH and at acid pH were tested. In addition, some testing was also undertaken with Na insulin.

The tests were conducted using plastic tybes (5 ml test tubes, Sarstedt, sealed by plastic caps covered with paraffin) each containing 2 ml of the insulin solutions noted below. The tubes were continuously agitated in a metabolic shaking incubator (Dubnoff E.C.A. Co.) at 60 to 80 r.p.m. and 37° C. for periods up to sixteen days.

The zinc insulin solutions were prepared by appropriate dilutions of highly concentrated (500 U/ml) single component, neutral, pork, zinc-insulin (U.500 regular Iletin II., Eli Lilly & Company). The unbuffered diluting fluid contained glycerin, 16 mg/ml, and phenol, 2 mg/ml of distilled water (Eli Lilly & Company). Either sodium hydroxide or hydrochloric acid was added if necessary to adjust the pH to 7.5 for neutral insulin solutions or to 2.8 to 3.5 for acid insulin solutions. Final insulin concentration in all solutions was 50 U/ml (2 mg/ml).

The sodium insulin solutions were made by dissolving pork sodium-insulin crystals (U.1000 neutral sodium insulin special pork obtained from Eli Lilly & Company) in the same diluting fluid as utilized with the zinc insulin. The solutions were adjusted to neutral or acid pH as indicated above. Final insulin concentration in all solutions was 2 mg/ml (50 U/ml).

Insulin solutions with amino acid added were prepared by addition of the dry amino acids (Sigma Company) to the neutral zinc or sodium insulin solutions. Final concentration of the amino acid additives was 7 mg per ml of insulin solution. pH was adjusted, when necessary, to 7.5 for neutral insulin mixtures and to 3.3–3.5 for acid insulin mixtures.

Several non-amino carboxylic acids, i.e., lactic acid, acetic acid, and citric acid, were added under the same conditions of concentration and pH as described for the amino acids.

The various insulin solutions, both as made up without additives and with additives, were shaken as noted above for up to sixteen days, at which time the solutions were examined with an optical densitometer at a wave length 600 nm. The optical density (OD) of each solution was an indication of the amount of aggregation present after the shaking period. The higher the optical density, the greater the aggregation in that solution.

Table I below summarizes the various zinc insulin solutions studied and the resultant optical densities thereof at the end of the shaking period.

TABLE I

Summation of Shaking Experiments Using
Neutral Single Component Zinc Insulin (Eli Lilly & Company)
Time = 16 days

| Agent Added | Number of Experiments | Number of Tubes | pH | Optical Density ± 1 × SE |
|---|---|---|---|---|
| None | 6 | 21 | 7.4 | 0.603 ± 0.08 |
| Albumin (5%) | 2 | 6 | 7.4 | 0.49 ± 0.05 |
| None | 4 | 11 | 2.9–3.3 | 0.181 ± 0.03 |
| Glutamic Acid | 2 | 9 | 7.4 | 0.717 ± 0.266 |
| Glutamic Acid | 6 | 17 | 3.3–3.5 | 0.123 ± 0.02 |
| Aspartic Acid | 1 | 3 | 7.4 | 0.51 ± 0.078 |
| Aspartic Acid | 4 | 7 | 3.3–3.5 | 0.084 ± 0.009 |
| Glycine | 1 | 2 | 7.4 | 0.66 ± 0.095 |
| Glycine | 1 | 2 | 3.3–3.5 | 0.28 ± 0.04 |
| Lysine | 1 | 2 | 7.4 | 0.25 ± 0.08 |
| Lysine | 1 | 2 | 3.3–3.5 | 0.35 ± 0.13 |
| Alanine | 3 | 5 | 7.4 | 0.84 ± 0.04 |
| Alanine | 1 | 2 | 3.3–3.5 | 0.41 ± 0.02 |
| Cysteine | 1 | 2 | 7.4 | 0.34 ± 0.13 |
| Cysteine | 1 | 2 | 3.3–3.5 | 0.39 ± 0.08 |
| Asparagine | 1 | 2 | 7.4 | 0.87 ± 0.13 |
| Glutamine | 1 | 2 | 7.4 | 0.68 ± 0.03 |
| Valine | 1 | 2 | 7.4 | 0.64 ± 0.26 |
| Serine | 1 | 2 | 7.4 | 0.89 ± 0.02 |
| Threonine | 1 | 2 | 7.4 | 0.76 ± 0.02 |
| Methionine | 1 | 2 | 7.4 | 0.74 ± 0.22 |
| Arginine | 1 | 2 | 7.4 | 0.074 ± 0.03 (Gel formed) |
| Phenyl Alanine | 1 | 2 | 7.4 | 0.685 ± 0.09 |
| Tryptophane | 1 | 2 | 7.4 | 0.585 ± 0.200 |
| Proline | 1 | 2 | 7.4 | 0.665 ± 0.21 |
| Leucine | 1 | 2 | 7.4 | 0.695 ± 0.03 |
| Histidine | 1 | 2 | 7.4 | 0.245 ± 0.08 |
| Lactic Acid | 1 | 3 | 3.3–3.5 | heavy precipitate |
| Citric Acid | 1 | 3 | 3.3–3.5 | heavy precipitate |
| Acetic Acid | 1 | 3 | 3.3–3.5 | heavy precipitate |

Table II below is similar to Table I, except Na insulin solutions were tested. Only a limited number of Na insulin solutions were included in the study.

TABLE II

Summation of Shaking Experiments
Using Na Insulin (Eli Lilly & Company)

| Agent Added | Number of Experiments | Number of Tubes | pH | Optical Density ± 1 × SE |
|---|---|---|---|---|
| None | 2 | 7 | 7.4 | 0.18 ± 0.02 |
| None | 1 | 5 | 3.5 | 0.128 ± 0.02 |
| Glutamic Acid | 3 | 10 | 3.5 | 0.13 ± 0.03 |
| Aspartic Acid | 1 | 3 | 3.5 | 0.10 ± 0.01 |

The data presented in Tables I and II above and observations made during the shaking tests revealed a number of significant facts:

(1) The deviation in observed optical density from tube to tube indicated a high variability, suggesting that the microsurfaces of the plastic tubes can influence aggregation.

(2) In neutral solutions (pH=7.4) aggregates appeared by the fourth day and progressively increased through the sixteenth day. When examined by microscope, the aggregates included typical insulin crystals, aggregated crystals, and apparent fibrils.

(3) Aggregates of acidified (pH 2.9–3.3) neutral zinc insulin, unbuffered, appeared by the fourth day; and the aggregation was as great through day 16 as unacidified solutions.

(4) Glutamic and aspartic acids at pH 3.3–3.5, their aproximate isoelectric points, prevented the development of any appreciable aggregation throughout the entire experiment. Such amino acids, however, do not offer any effective protection at neutral pH's. Aspartic acid was more effective than glutamic acid; however, aspartic acid is less soluble in insulin solutions at acid pH's than is glutamic acid. All other amino acids tested were not nearly as effective as the aspartic acid and glutamic acid.

(5) Non-amino organic acids such as lactic acid, citric acid, and acetic acid do not prevent aggregation even at pH 3.3–3.5.

(6) From Table II it will be noted that Na insulin at pH 7.4 also aggregates. By 16 days, aggregation is less than that seen for neutral zinc insulin at the same pH. Aggregation of Na insulin at pH 3.3–3.5 is less than at pH 7.4 but is nevertheless appreciable. The results also indicate some protective effect of Na insulin solutions by aspartic acid at acid pH.

(7) Acid pH alone, in the absence of buffer, is relatively effective in reducing aggregation; however, the presence of buffer agents, e.g., monocarboxylic amino acids, citrate, lactate, and acetate, exacerbate aggregation. Although exhibiting reduced aggregation, unbuffered acid insulin solutions are not desired because they may be pH labile over extended periods of time, particularly in systems which must necessarily be connected to body tissues and fluids.

One advantage of the aspartic acid and glutamic acid addition to insulin solutions, is their ability to maintain the solution's acid pH's over long periods of time. Thus in a in vivo situation, the addition of aspartic acid, or glutamic acid, to insulin solutions, is indicated for the reduction of aggregation.

EXAMPLE 2

IN VITRO TESTING

Controlled Shaking of Insulin Solutions in 2-Week Minipumps Equipped with Small Diameter Catheters.

Minipumps (Alzet Osmotic Minipump No. 2002, Alza Corporation, Palo Alto, Calif.) that release their contents (213.7±94 ml) at a constant rate (0.47±0.02 ml/hr) over a minimum of 14 days were filled with insulin or amino acid-insulin solutions. The minipumps were weighed before and after filling to determine the initial inner fluid volume. A 5 cm vinyl catheter (Iv. soft medical polyvinyl tubing; i.D. = 0.023 inch; Bolab Inc. Co., Derry, N.H.) was attached to the tubes' exterior beyond their flanges.

Acid and neutral insulin solutions were prepared with and without glutamic or aspartic acids as described in Example I except insulin concentrations were 120 U/ml (approximately 5 mg/ml). Glutamic and aspartic acids were added to a concentration of 7 mg/ml. The final pH's of the amino acid insulin solutions were 3.3–3.5.

Pumps with attached catheters were placed in a 5 ml plastic vial containing a cotton wad and sufficient saline to immerse and activate the pump. The catheter passed through a 0.5 ml air space at the top of the fluid in the tube, the terminal end being submerged in the saline. The tubes were sealed with a plastic cap covered with parafilm. They were shaken at 37° in a metabolic shaking incubator (Dubnoff E.C.A.) at 80–100 r.p.m. for periods up to 8 days. Pumps were removed from the tubes on the 8th day after shaking; catheters were examined for precipitates by eye and residual contents were removed and centrifuged in microtubes to evaluate the precipitate.

Table III below presents the results of the minipump shaking tests:

TABLE III

Stability of Single Component Zinc Insulin (Eli Lilly & Company) Shaken 8 days in Minipumps

| Insulin Preparations | Number of Pumps | Number of Pumps with Precipitates | Number of Pumps with Aggregates in Catheter |
| --- | --- | --- | --- |
| Zinc-insulin (pH, 7.4) | 3 | 3 | 3 |
| Zinc-insulin (pH, 3.3 | 6 | 0 | 4 |
| Glutamic acid-Zinc-insulin (pH, 3.3) | 6 | 0 | 0 |

EXAMPLE 3

IN VIVO TESTING

Continuous Provision of Insulin Solutions in 2-Week Minipumps Placed Subcutaneously or Intraperitoneally in Genetically Diabetic Ambulatory Chinese Hamsters.

Two-week minipumps (Alza Corporation) like those discussed in Example 2 above were filled with diluted neutral pork zinc insulin (u.500 regular Iletin II, Eli Lilly & Company). In some samples glutamic acid was added and pH was adjusted to neutral (7.4). In other samples the pH was allowed to remain at 2.8 to 3.5. Final insulin concentration averaged 129 U/ml (approx. 5 mg/ml) and daily delivery rate was 57 units/day at a flow rate of 0.5 ul/hr. Additional samples were prepared as controls. These minipumps contained insulin + saline.

Diabetic Chinese hamsters of both sexes, matched for weight and age were obtained through the Chinese Hamster Program Project (Kalamazoo, Mich.). These animals had been bred for 15-20 generations for non-obese diabetes characterized by impaired insulin secretion, excessive glucagon secretion and some peripheral resistance to insulin. Insulin doses were determined from previous studies with the 7-day Alzet minipump (Frankel and Grodsky, Diabetes 28:544, 1979; Frankel, Schmid, and Grodsky, Endocrinolgy 104:1532–1539, 1979). Only diabetic hamsters with fed plasma glucose levels exceeding 220 mg/dl were in the experiment.

The pumps were placed subcutaneously in the animals through a 2 cm. incision made in the skin of the neck. For subcutaneous experiments a 2 cm. catheter was left exposed to drain in the subcutaneous space. For intraperitoneal experiments, a 5 cm catheter was attached to the minipump and directed internally to the peritoneum where it was surgically affixed to drain continuously into the peritoneal cavity.

The pumps were removed on the 14th day after implant and the residual contents were cenrifuged in microtubes to evaluate the precipitate, if any. Blood for glucose determinations was drawn without anesthesia from the orbital sinus.

The experimental system described herein has particularly sensitive to aggregation of the insulin because of the exceedingly low flow rate from the minipumps; the elevated temperature (34°); the concentrated insulin solutions used; and the continuous activity of the ambulatory hamsters. The results of these tests are shown in FIGS. 1 and 2 of the drawing.

Figure 2:
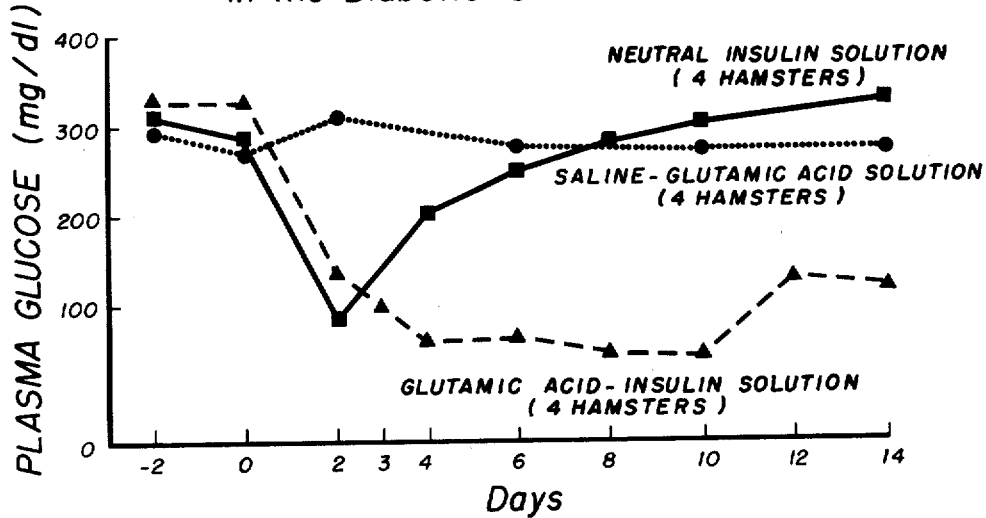
FIG. 2 is a graph presenting data gathered from the intraperitoneal delivery of unprotected insulin solutions, and glutamic acid protected insulin solutions, as well as control glutamic acid-saline solutions, to genetrically diabetic Chinese hamsters by means of implanted minipumps over a 14 day period.

From a review of both FIGS. 1 and 2, it is evident that there was no significant difference when the minipumps delivered their solutions subcutaneously or intraperitoneally. It is significant, however, that the glutamic acid protected insulin solutions maintained a lower plasma glucose level over the entire 14 day trial period; while the unprotected insulin solutions exhibited an impaired ability to adequately maintain low plasma glucose levels beyond 3 or 4 days. It must be concluded that aggregation in the unprotected minipumps impaired the delivery of insulin to the subject beyond the 3 or 4 day period. Obviously freedom from aggreation in the glutamic acid protected minipumps permitted adequate delivery of insulin to the subject over the entire 14 day period.

All the minipumps were removed from the test subjects and examined. All minipumps were similarly depleted of liquid. In all cases where glucose control was not maintained, precipitates were observed in the pumps and in the catheter. Where protection was maintained pump and catheter contents were water clear.

The Examples set forth above indicate that multi-carboxylic amino acids, when added to insulin solutions at pH's approximating the isoelectric point of the amino acids, prevent or greatly decrease the tendency of insulin solutions to form aggregates. Glutamic acid and aspartic acid, being naturally occurring amino acids utilized in mammalian metabolic processes, are pharmaceutically acceptable for addition to insulin solutions. However, it is expected that related multi-carboxylic acids having amino functionalities would also exhibit such anti-aggregation.

Although chelation with insulin has not been shown to be determinative of the protective effects; such related compounds may very well exhibit chelating abilities with insulin.

The foregoing description of the invention has been presented for purposes of illustration. It is not intended to be exhaustive or to limit the invention to the exact anti-aggregation agents or protected insulin solutions disclosed, and obviously many modifications and variations are possible in light of the above description. All obvious modifications and variations of the invention are intended to be included herein and to fall within the scope of the claims appended hereto.

We claim:

1. A method of reducing the aggregation of insulin in a solution which is retained over extended periods of time in a reservoir under agitation and at about body temperature comprising admixing into said insulin solution an effective amount of an anti-aggregation agent having two carboxyl moieties and at least one amino or amino derivative moiety, and adjusting the pH of said insulin solution to a pH at about the isoelectric point of the anti-aggregation agent.

2. The method of claim 1 wherein said organic anti-aggregation agent is a di-carboxylic amino acid or a derivative of a di-carboxylic amino acid.

3. The method of claim 2 wherein said agent is glutamic acid.

4. The method of claim 2 wherein said agent is aspartic acid.

5. The method of claim 1 wherein the pH of said insulin solution is at an acid pH.

6. The method of claim 3 wherein the pH of said insulin solution is from about 3 to 3.5.

7. The method of claim 4 wherein the pH of said insulin solution is from about 3 to 3.5.

8. A stabilized insulin aqueous solution for use at about body temperature and under agitation consisting essentially of insulin, water, and an anti-aggregation agent having two carboxyl moieties and at least one amino or amino derivative moiety, the pH of said solution being within about the range of the isoelectric point of said anti-aggregation agent.

9. The stabilized solution of claim 8 wherein the anti-aggregation agent is glutamic acid.

10. The stabilized solution of claim 8 wherein the anti-aggregation agent is aspartic acid.

11. The stabilized solution of claim 9 wherein the solution is at a pH of from about 3 to 3.5.

12. The stabilized solution of claim 10 wherein the solution is at a pH of from about 3 to 3.5.

* * * * *